(12) United States Patent
Peng et al.

(10) Patent No.: US 12,007,513 B2
(45) Date of Patent: Jun. 11, 2024

(54) METHOD AND APPARATUS FOR IMPROVED PHOTOSENSOR LIGHT COLLECTION IN A RADIATION DETECTOR

(71) Applicant: CANON MEDICAL SYSTEMS CORPORATION, Otawara (JP)

(72) Inventors: Peng Peng, Vernon Hills, IL (US); Yi Qiang, Vernon Hills, IL (US); Xiaoli Li, Vernon Hills, IL (US); Kent C. Burr, Vernon Hills, IL (US); Manabu Teshigawara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/581,005

(22) Filed: Jan. 21, 2022

(65) Prior Publication Data

US 2023/0236328 A1  Jul. 27, 2023

(51) Int. Cl.
*G01T 1/20* (2006.01)
*A61B 6/03* (2006.01)
*A61B 6/42* (2024.01)
*G01T 1/164* (2006.01)
*G01T 1/29* (2006.01)

(52) U.S. Cl.
CPC .......... *G01T 1/1642* (2013.01); *A61B 6/037* (2013.01); *A61B 6/4258* (2013.01); *G01T 1/1644* (2013.01); *G01T 1/2018* (2013.01); *G01T 1/2985* (2013.01)

(58) Field of Classification Search
CPC ... G01T 1/1642; G01T 1/1644; G01T 1/2018; G01T 1/2985; A61B 6/037; A61B 6/4258
See application file for complete search history.

(56) References Cited

U.S. PATENT DOCUMENTS

| | | | |
|---|---|---|---|
| 8,357,903 B2 * | 1/2013 | Wang | G01T 1/2985 250/362 |
| 9,864,073 B1 * | 1/2018 | Kim | G01T 1/202 |
| 2007/0248307 A1 * | 10/2007 | Page | G02B 6/0065 65/392 |
| 2010/0012846 A1 * | 1/2010 | Wang | G01T 1/1642 250/363.04 |

* cited by examiner

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

A method and apparatuses for a radiation detector apparatus, comprising a scintillator array comprising a plurality of scintillator crystals. The plurality of scintillator crystals includes a first scintillator crystal and a second scintillator crystal adjacent to the first scintillator crystal within the scintillator array. A photosensor array comprising a plurality of photosensors including a first photosensor configured to detect photons from the first scintillator crystal. A first separator positioned between the first scintillator crystal and the second scintillator crystal. First separator optically separates the first scintillator crystal and the second scintillator crystal such that the first photosensor detects photons from the first scintillator crystal and not from the second scintillator crystal.

14 Claims, 17 Drawing Sheets

600

```
┌─────────────────────────────────────────────────────────────────────────────┐
│ Receiving incident radiation at a scintillator crystal of a scintillator array comprising a plurality │
│                             of scintillator crystals                       602 │
└─────────────────────────────────────────────────────────────────────────────┘
                                      ↓
┌─────────────────────────────────────────────────────────────────────────────┐
│ Converting a portion of energy from the radiation including photons to generate scintillation │
│                                      light                                 604 │
└─────────────────────────────────────────────────────────────────────────────┘
                                      ↓
┌─────────────────────────────────────────────────────────────────────────────┐
│ Reflecting the photons in a light guide by a reflective film from a first scintillator pixel to a first │
│ photo sensor, such that a first photo sensor is positioned optically opposite to a first scintillator │
│                                      pixel                                 606 │
└─────────────────────────────────────────────────────────────────────────────┘
                                      ↓
┌─────────────────────────────────────────────────────────────────────────────┐
│ Detecting the photons from the first scintillator pixel by the first photo sensor, such that first │
│ photo sensor detects photons from the first scintillator pixel and not from the neighboring │
│                              scintillator pixels                           608 │
└─────────────────────────────────────────────────────────────────────────────┘
```

FIG. 5

METHOD AND APPARATUS FOR IMPROVED PHOTOSENSOR LIGHT COLLECTION IN A RADIATION DETECTOR

FIELD OF THE INVENTION

Embodiments described herein relate generally to an improved photosensor light collection in a radiation detector, specifically to a method and apparatus for scintillation light collection in a radiation detector.

DESCRIPTION OF THE RELATED ART

The background description provided herein is for the purpose of generally presenting the context of the disclosure. Work of the presently named inventors (to the extent the work is described in this background section) as well as aspects of the description that may not otherwise qualify as prior art at the time of filing are neither expressly nor impliedly admitted as prior art against the present disclosure.

Conventionally, medical image diagnosis apparatuses configured to generate a medical image of an examined subject by using radiation are known, including X-ray Computed Tomography (CT) apparatuses, Positron Emission Tomography (PET) apparatuses, Single Photon Emission Computed Tomography (SPECT) apparatuses, and gamma cameras, among others. Such medical image diagnosis apparatuses include a radiation detector configured to detect radiation such as X-rays or γ-rays.

Some radiation detectors include a scintillator array configured to emit light (scintillation light) in response to radiation becoming incidence thereto; and a Photodiode Array (PDA) configured to output electrical signals in accordance with the scintillation light. The scintillator array and the PDA function in units of a plurality of detecting elements arranged in a channel direction and a slice direction. A plurality of scintillator arrays and a plurality of PDAs are installed in a radiation detector in the form of detector packages, each of which is a unit that can be replaced when a failure occurs.

In positron emission tomography (PET) imaging, a tracer agent is introduced into the patient, and the physical and bio-molecular properties of the agent cause it to concentrate at specific locations in the patient's body. The tracer emits positrons, resulting in an annihilation event that occurs when the positron collides with an electron and produces two gamma rays (at 511 keV) traveling at substantially 180 degrees apart.

PET imaging systems use detectors positioned around the patient to detect coincidence pairs of gamma rays. A ring of detectors can be used in order to detect gamma rays coming from each angle. Thus, a PET scanner can be substantially cylindrical to maximize the capture of the isotropic radiation. A PET scanner can be composed of several thousand individual crystals (e.g., Lutetium Orthosilicate (LYSO) or other scintillating crystals) which are arranged in two-dimensional scintillator arrays that are packaged in modules with photodetectors to measure the light pulses from respective scintillation events. For example, the light from respective elements of a scintillator crystal array can be shared among multiple photomultiplier tubes (PMTs) or can be detected by silicon photomultipliers (SiPMs) having a one-to-one correspondence with the elements of a scintillator crystal array. To reconstruct the spatial-temporal distribution of the tracer via tomographic reconstruction principles, each detected event is characterized for its energy (i.e., amount of light generated), its location, and its timing. By detecting the two gamma rays, and drawing a line between their locations (i.e., by generating the line-of-response (LOR)), one can determine the likely location of the original disintegration. The timing information can also be used to determine a statistical distribution for the annihilation along the LOR based on time-of-flight (TOF) information of the two gamma rays. By accumulating a large number of LORs, tomographic reconstruction can be performed to determine a volumetric image of the spatial distribution of radioactivity (e.g., tracer density) within the patient.

Single-photon emission computed tomography (SPECT) is similar to PET except a collimator is used to restrict the angle of gamma rays incident on the respective detector elements (e.g., the respective elements in the scintillator crystal array), making reconstruction possible using single gamma-ray detection events as opposed to requiring coincidences to determine a LOR.

In addition to position information (e.g., the LOR) and timing information (e.g., the TOF), detectors in PET and SPECT systems can also acquire and use energy information in the image reconstruction process. However, energy measurements can deviate from an ideal linear response due to non-linearities in the measurement process (e.g., saturation effect of photo detectors, or light yield non-proportionality of the scintillation crystals) and/or practical considerations (e.g., related to light/charge sharing among channels during a multi-channel gamma-ray detection (e.g., due to the gamma-ray energy being absorbed in multiple detectors/channels as can happen due to Compton scattering)).

In the context of the above, it is desirable to provide improved energy calibrations for gamma-ray detectors. Accordingly, the methods and structures described herein provide for improved scintillation light collection in a radiation detector.

SUMMARY OF THE INVENTION

Disclosed is a radiation detector apparatus, including, but not limited to: (a) a scintillator array including, but not limited to, a first scintillator crystal and a plurality of second scintillator crystals adjacent to the first scintillator crystal within the scintillator array; (b) a photosensor array including, but not limited to, a first photosensor which is coupled in a one-to-one relationship with the first scintillator crystal; and (c) a first separator positioned between the first scintillator crystal and the plurality of second scintillator crystals, wherein the first separator optically separates the first scintillator crystal and the plurality of second scintillator crystals such that the first photosensor detects photons from the first scintillator crystal and not from the plurality of second scintillator crystals in the scintillator array.

In one aspect, the radiation detector apparatus further includes, but is not limited to, a light-guide, positioned between the scintillator array and the photosensor array, wherein the first separator is positioned within the light-guide between the first scintillator crystal and the plurality of second scintillator crystals.

In one aspect, the plurality of second scintillator crystals includes, but is not limited to, a second scintillator crystal and a third scintillator crystal, and the first scintillator crystal and the second scintillator crystal are adjacent to each other in a first direction and the first scintillator crystal and the third scintillator crystal are adjacent to each other in a second direction perpendicular to the first direction.

In one aspect, the radiation detector apparatus further includes, but is not limited to, a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

In one aspect, the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, opaque particles (such as $BaSO_4$ powder), and a reflective film.

Disclosed also is a medical image diagnosis apparatus including, but not limited to: (a) a scintillator array including, but not limited to, a first scintillator crystal and a plurality of scintillator crystals adjacent to the first scintillator crystal within the scintillator array; (b) a photosensor array including, but not limited to, a first photosensor which is coupled in a one-to-one relationship with the first scintillator crystal; and (c) a first separator positioned between the first scintillator crystal and the plurality of second scintillator crystals, wherein the first separator optically separates the first scintillator crystal and the plurality of second scintillator crystals such that the first photosensor detects photons from the first scintillator crystal and not from the plurality of second scintillator crystals in the scintillator array.

In one aspect, the medical image diagnosis apparatus further includes, but is not limited to, a light-guide, positioned between the scintillator array and the photosensor array wherein the first separator is positioned within the light-guide between the first scintillator crystal and the plurality of second scintillator crystals.

In one aspect, the plurality of second scintillator crystals includes, but is not limited to, a second scintillator crystal and a third scintillator crystal, and the first scintillator crystal and the second scintillator crystal are adjacent to each other in a first direction and the first scintillator crystal and the third scintillator crystal are adjacent to each other in a second direction perpendicular to the first direction.

In one aspect, the medical image diagnosis apparatus further includes, but is not limited to, a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

In one aspect, the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, opaque particles (such as $BaSO_4$ powder), and a reflective film.

Disclosed also is a method of an improved photosensor light collection, the method comprising: (a) receiving incident radiation by a scintillator array comprising a first scintillator crystal and a plurality of scintillator crystals adjacent to the first scintillator crystal within the scintillator array; (b) detecting photons by a photosensor array from the first scintillator crystal, wherein the photosensor array comprising a first photosensor which is coupled in a one-to-one relationship with the first scintillator crystal; and (c) positioning a first separator between the first scintillator crystal and the plurality of second scintillator crystals. The first separator is configured to optically separate the first scintillator crystal and the plurality of second scintillator crystals such that the first photosensor detects photons from the first scintillator crystal and not from the plurality of second scintillator crystals in the scintillator array.

In one aspect, the plurality of second scintillator crystals includes, but is not limited to, a second scintillator crystal and a third scintillator crystal, and the first scintillator crystal and the second scintillator crystal are adjacent to each other in a first direction and the first scintillator crystal and the third scintillator crystal are adjacent to each other in a second direction perpendicular to the first direction.

In one aspect, the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, opaque particles (such as $BaSO_4$ powder), and a reflective film.

BRIEF DESCRIPTION OF THE DRAWINGS

A more complete understanding of this disclosure is provided by reference to the following detailed description when considered in connection with the accompanying drawings, wherein:

FIG. 5 is a flowchart illustrating an example of a method for improved photosensor light collection in a radiation detector according to an exemplary embodiment;

DETAILED DESCRIPTION OF THE PREFERRED EMBODIMENTS

According to one aspect disclosed herein, a radiation detector apparatus, a medical image diagnosis apparatus, and a method of an improved photosensor light collection are provided for an improved photosensor light collection in a radiation detector that has high reliability and will be explained below, with reference to the accompanying drawings.

Figure 1:
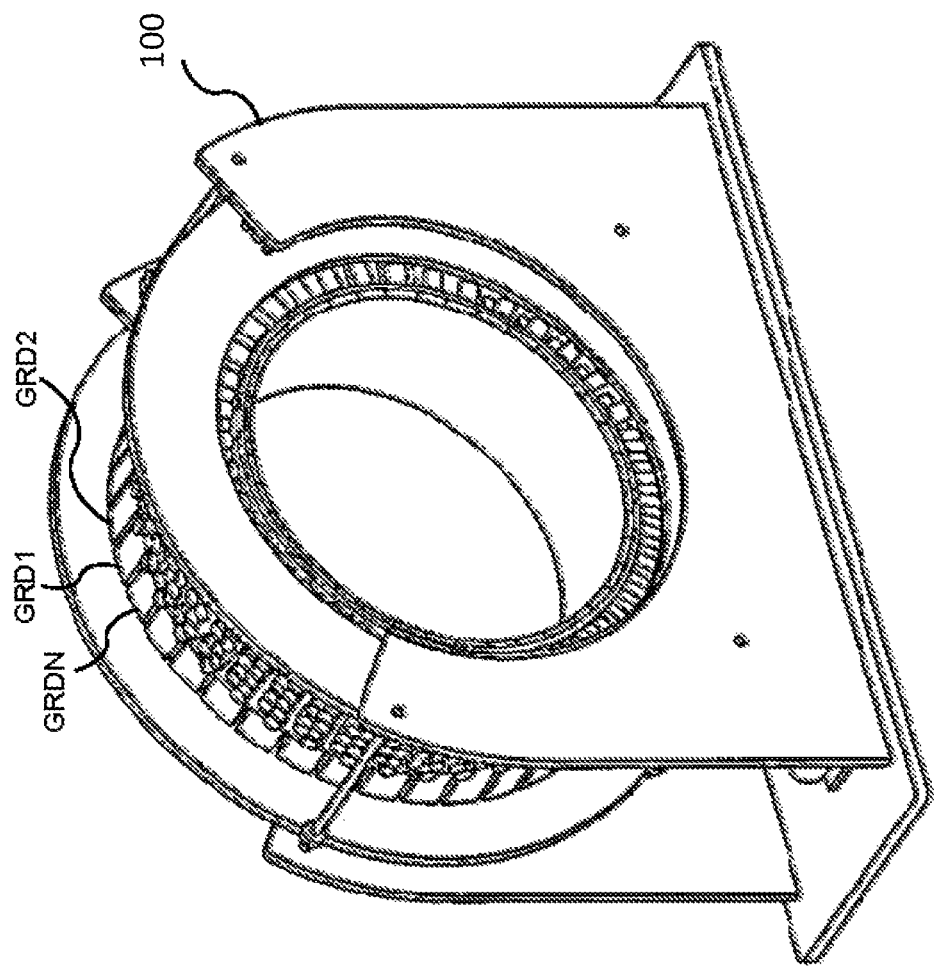
FIG. 1 shows a perspective view of a positron-emission tomography (PET) scanner, according to an embodiment of the present disclosure.
Figure 2:
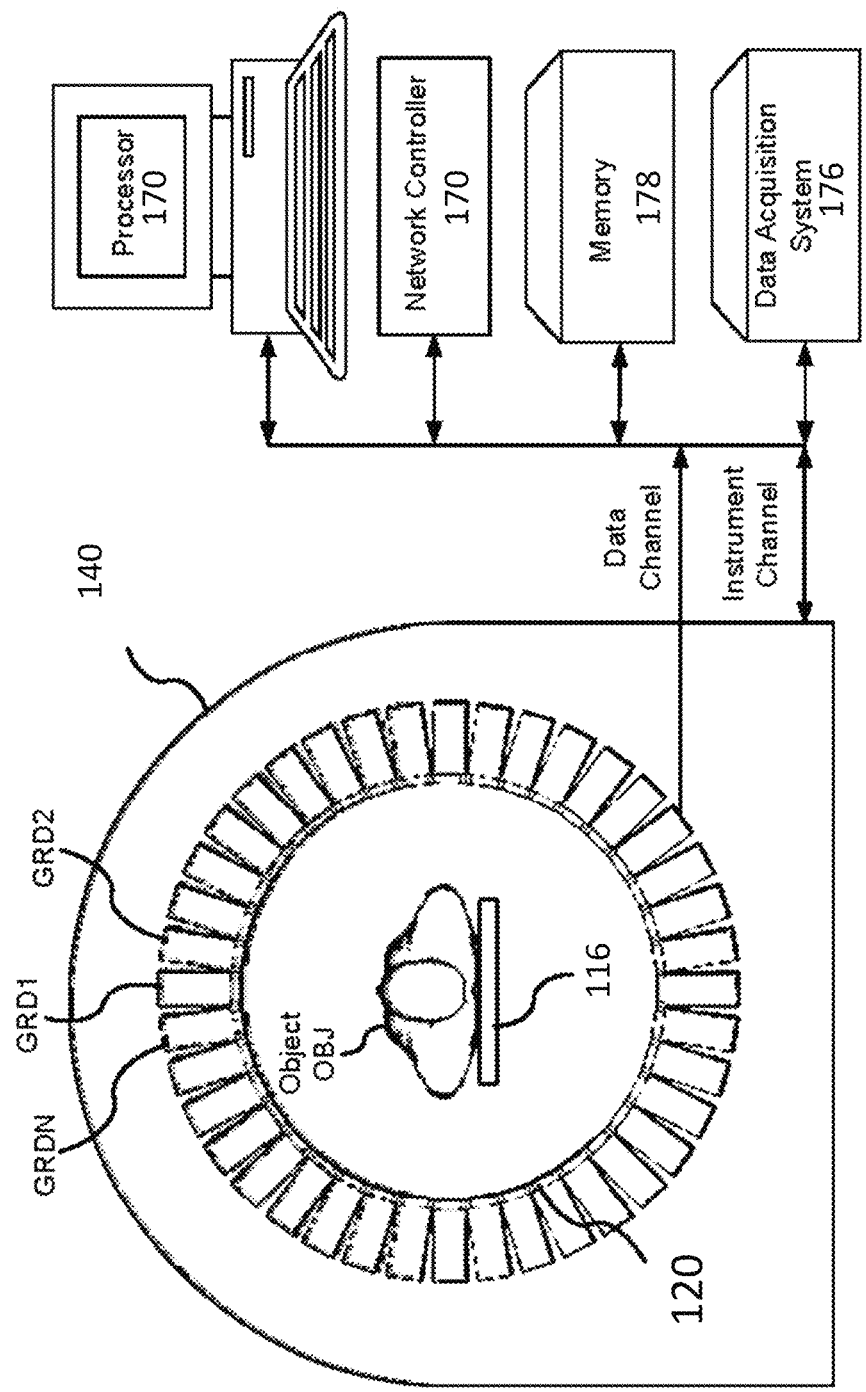
FIG. 2 shows a schematic view of a PET scanner, according to an embodiment of the present disclosure.

FIGS. 1 and 2 show a non-limiting example of a PET scanner 100 that can implement the methods described herein. The PET scanner 100 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 100.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 2 shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIG. 2. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 2 shows an example of the arrangement of the PET scanner 100, in which the object OBJ to be imaged rests on a table 116 and the GRD modules GRD1 through GRDN are arranged circumferentially around the object OBJ and the table 116. The GRDs can be fixedly connected to a circular component 120 that is fixedly connected to the gantry 1140. The gantry 140 houses many parts of the PET imager. The gantry 140 of the PET imager also includes an open aperture through which the object OBJ and the table 116 can pass, and gamma-rays emitted in opposite directions from the object OBJ due to an annihilation event can be detected by the GRDs and timing and energy information can be used to determine coincidences for gamma-ray pairs.

In FIG. 2, circuitry and hardware is also shown for acquiring, storing, processing, and distributing gamma-ray detection data. The circuitry and hardware include: a processor 170, a network controller 174, a memory 178, and a data acquisition system (DAS) 176. The PET imager also includes a data channel that routes detection measurement results from the GRDs to the DAS 176, the processor 170, the memory 178, and the network controller 174. The DAS 176 can control the acquisition, digitization, and routing of the detection data from the detectors. In one implementation, the DAS 176 controls the movement of the bed 116. The processor 170 performs functions including reconstructing images from the detection data, pre-reconstruction processing of the detection data, and post-reconstruction processing of the image data, as discussed herein.

The processor 170 can be configured to perform various steps of the methods described herein and variations thereof. The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 170 can execute a computer program including a set of computer-readable instructions that perform various steps of the methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a i3, i5, i7, i9, or Xenon processor from Intel of America or a Ryzen or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the PET imager. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 5G and 4G wireless cellular systems. The wireless network can also be WiFi, Bluetooth, or any other wireless form of communication that is known.

Figure 3:
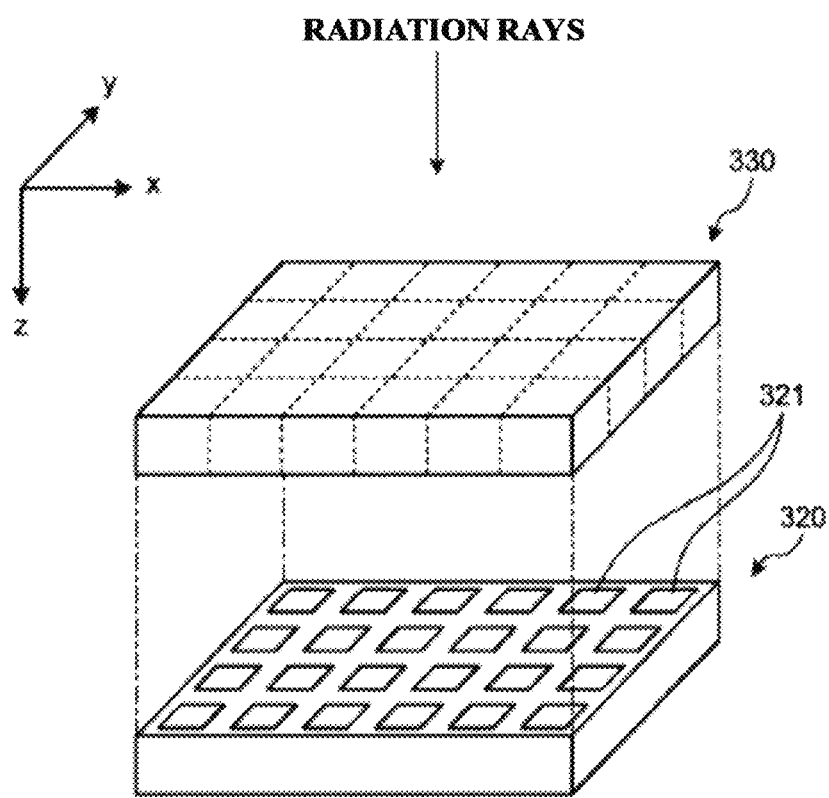
FIG. 3 shows a diagram of a gamma-ray detector module having multiple scintillator crystal elements arranged as an array and using silicon photomultipliers (SiPMs) as photodetectors.

In FIG. 3, the scintillator is cut into a periodic array of separate crystals separated and optically isolated by reflective barriers between the individual elements of the crystal array. This optical isolation between crystals in the block can be imperfect allowing some light sharing between adjacent crystals. FIG. 3 shows the case when silicon photomultipliers (SiPMs) are provided with a one-to-one correspondence between the individual elements of the crystal array and the respective SiPMs. Alternatively, the photodetectors can be other types of detectors (photomultiplier tubes (PMTs), avalanche photodiodes (APDs), silicon photomultipliers (SiPMs)), in which case there is often many more crystal elements than photodetectors (i.e., a many-to-few correspondence between crystal elements and photodetectors). When the photodetectors are other types of detectors, the light sharing between adjacent crystals can be small compared to light sharing that occurs after exiting the crystals, in which case, scintillation events can be distinguished between individual elements of the array using Anger arithmetic to approximately determine locations and then using a floodmap calibration to generate a lookup table mapping the approximate locations calculated using Anger arithmetic to respective indices of the crystal array.

In FIG. 3, the light from each crystal element is detected by a respective SiPM. With each crystal having its own photodetector, the light sharing among photodetectors can be reduced. Further, each crystal having its own photodetector can result in enhanced resolution by enabling discrimination between simultaneous scintillation events occurring at different crystals within a single detection module (e.g., utilizing Compton scattering information among adjacent crystals).

Figure 4A:
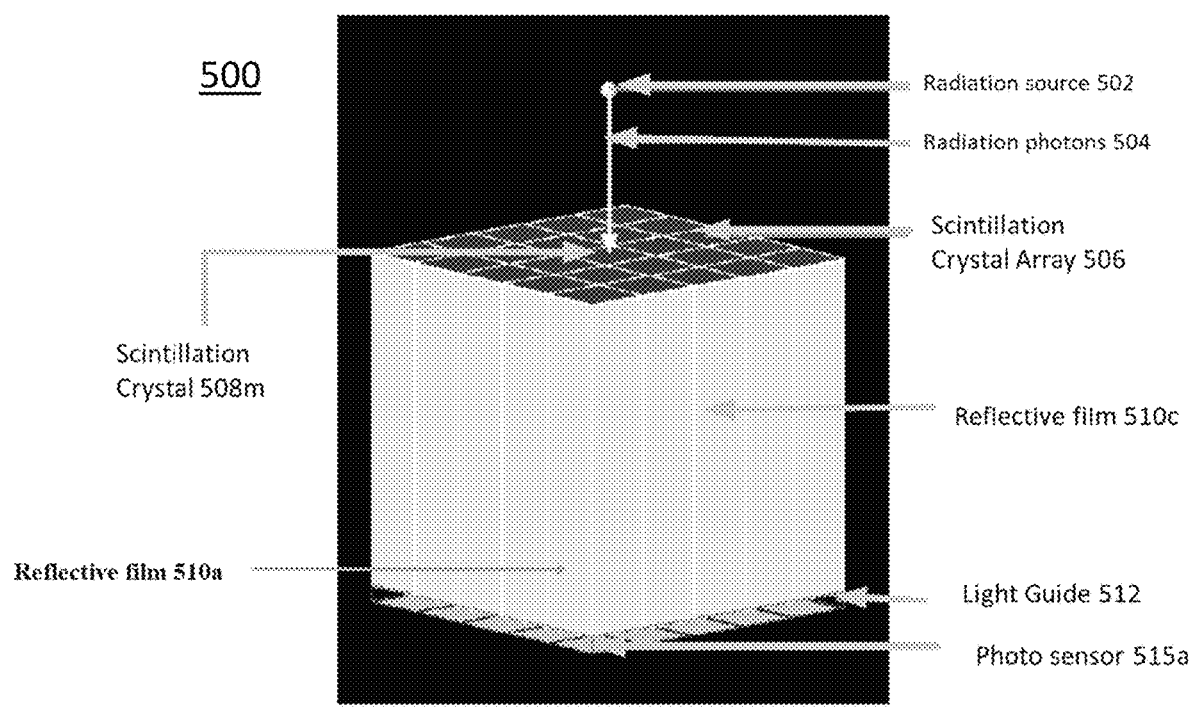
FIGS. 4A, 4B, 4C and 4D are drawings illustrating an example of a structure of a scintillator array including a region with an absence of reflective film.
Figure 4B:
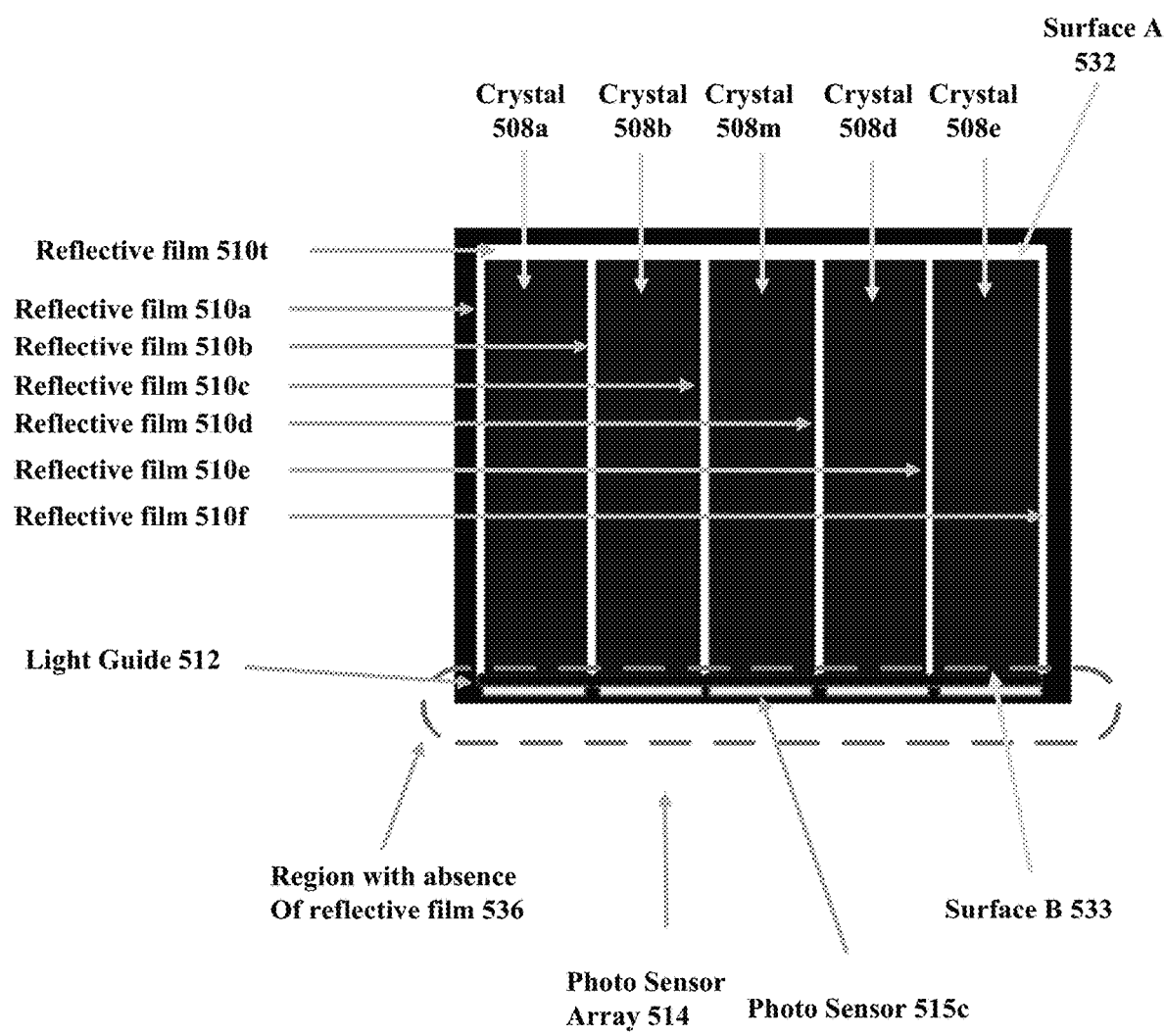

As illustrated in FIG. 4A, a radiation detector is illustrated as part of a positron emission tomography (PET) detector 500. FIG. 4A shows the PET detector 500 receiving radiation photons 504 from a radiation source 502. The radiation photons 504 enter the middle exemplary scintillation crystal 508m, although radiation photons actually impinge typically all of the scintillation crystals $508_x$ at some point within the scintillation crystal array 506, where "x" is a generic subscript representing any of the scintillation crystals. (Although the scintillation crystal array 506 is illustrated as having a structure of 5×5 scintillation crystals $508_x$, other configurations of rows and columns of scintillation crystals are possible within an array 506, and the number of rows need not equal the number of columns.) Further, FIG. 4A shows a number of reflective films (including reflective films labeled 510a and 510c), a light guide 512, and a photosensor array 514. FIG. 4B shows, a cross sectional view of the PET detector 500 (of FIG. 4A) and illustrates a plurality of reflective films 510a-510f surrounding a plurality of scintillation crystals 508a, 508b, 508m, 508d, and 508e of the scintillation crystal array 506 respectively. (Although scintillation crystal 508m is labeled "m" for "middle," it could have been labeled "508c" as an alternate nomenclature.) Each of the plurality of scintillation crystals 508a, 508b, 508m, 508d, and 508e are optically positioned such that each scintillation crystal is optically isolated from its neighboring scintillation crystal by the reflective films interposed therebetween. The radiation photons 504 illustrated as entering the scintillation crystal 508m of the scintillation crystal array 506 produces scintillation photons at a scintillation site within the crystal 508m.

Reflective films 510a-510f, and 510t may be made of an enhanced specular reflector (ESR) film, a glass material, a resin material, a deposited metallic silver material, a deposited aluminum material, and/or an adhesive material mixed with Teflon particles, although any other type of reflective film material may also be included.

In the illustrated exemplary embodiment, a light guide 512 is positioned in between the scintillation crystal array 506 and the photosensor array 514. The light guide 512 is utilized to distribute scintillation light generated from photons 504 and received from the scintillation crystal array 506 to the photosensor array 514 positioned at the bottom surface of FIG. 4A. The light guide 512 is a transparent layer made of transparent material such as glass or plastic, although any other type of transparent material may also be included. Alternatively, it is possible to have a gap between the scintillation crystal array 506 and the photosensor array 514 instead of a light guide.

The photosensor array 514 includes a plurality of individual photosensors 515. By way of example, the individual photosensors 515 may be silicon photomultipliers (SiPM) and the photosensor array 514 may be an array of a plurality of individual SiPMs. An SiPM is a solid-state single photon sensitive device that functions as a photosensor that detects photons. Each SiPM produces a current pulse in response to absorption of scintillation photons. Further, the PET detector 500 is designed such that each of the scintillation crystals 508a, 508b, 508m, 508d, and 508e in the scintillation crystal array 506 has a one-on-one optical coupling with a corresponding photosensor of the photosensor array 514.

A read-out method is provided such that upon the SiPM producing a current pulse in response to absorption of the scintillation photons, a timing signal is generated from the current pulse. Each SiPM outputs its own timing signal, and this timing signal is received by a Time-to-Digital Converter (TDC) (not shown).

FIG. 4B shows six reflective films 510a-510f arranged in a first direction along the side surfaces of the five scintillation crystals 508a, 508b, 508m, 508d, and 508e. Specifically, the reflective films 510b-510e are positioned in between the scintillation crystals 508a, 508b, 508m, 508d, and 508e of the scintillation crystal array 506 respectively in manner such that the reflective films 510a and 510f are positioned on the outer surface of the scintillation crystals 508a and 509e, respectively. Also, the reflective films 510a-510f start at a first end at the surface A 532 of the PET detector 500 where the scintillation crystals 508a, 508b, 508m, 508d, and 508e start and end at a second end at the surface B 533 which is where the scintillation crystals 508a, 508b, 508m, 508d, and 508e end and also where the light guide 512 layer starts. As illustrated in FIG. 4B, the scintillation crystals 508a, 508b, 508m, 508d, and 508e are also covered on their tops by a reflective film 510t where the "t" generally denotes the "top" reflective film.

In this embodiment, the reflective films 510a-510f terminate before the light guide 512 layer starts, illustrated by the absence of an extended reflective film in the region 536. Further, the radiation photons 504 enter into the scintillation crystal array 506 (through the surface A 532 shown in FIG. 4B) in a generally downward direction as shown in FIG. 4A. The scintillation light generated by a radiation photon travels through the scintillation crystal $508_x$ that it enters and is reflected by the reflecting films surrounding scintillation crystal $508_x$ and is directed towards the light guide 512. As would be understood, each scintillation crystal $508_x$ is actually surrounded by reflective films on 4 sides and on the top, and any one of those reflective films can guide scintillation light towards the light guide 512. The scintillation light then travels through the light guide 512a that is transparent and is received by a corresponding photosensor $514_x$ on the photosensor array 514. In the illustrated embodiment of FIGS. 4A and 4B, as the light guide 512 is a transparent layer (e.g., with a thickness of 0.5 mm), a portion of the scintillation light produced by a scintillation crystal $508_x$ may become spread out on the photosensor array 514 such that the scintillation light is received not only by the photosensor $515_x$ immediately below the scintillation crystal $508_x$ but also by at least one adjacent/neighboring photosensor $515_{x'}$ to the photosensor $515_x$ in the photosensor array 514. This spreading of scintillation light onto the adjacent/neighboring photosensors in the photosensor array 514 is referred to as optical light crosstalk.

Figure 4C:
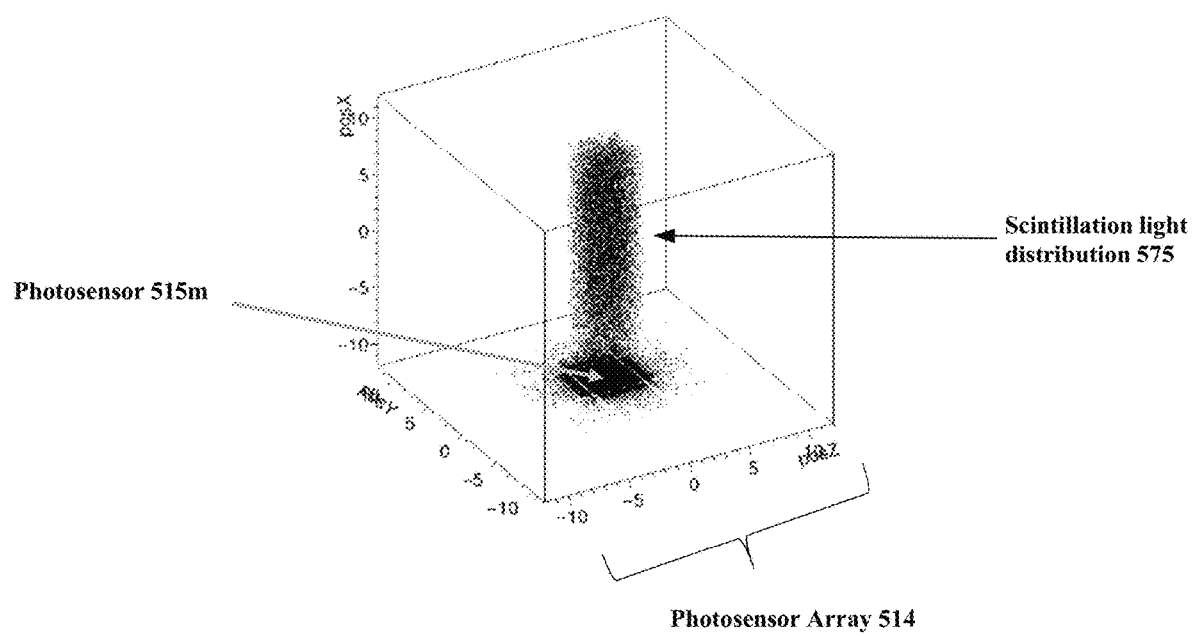

FIG. 4C shows an exemplary simulation graph of this optical light crosstalk produced by a simulation. The simulation graph illustrates a scintillation light distribution 575 generated in response to simulated radiation photons 504 (e.g., 511 keV gamma photons) hitting the middle scintillation crystal 508m to generate the scintillation light. Specifically, the scintillation light distribution 575 corresponding to radiation photons 504 (FIG. 4A) at a photosensor 515m has a one-to-one optical coupling with the scintillation crystal 515m. FIG. 4C also shows how the scintillation light is spread away from the photosensor 515m and received by neighboring photosensors on the photosensor array 514 in the form of optical light crosstalk. Accordingly, the optical light crosstalk will decrease the amount of light detected from a single scintillation crystal 508b, thereby degrading the timing/energy resolution and/or image quality of images generated from the gamma-ray radiations.

Figure 4D:
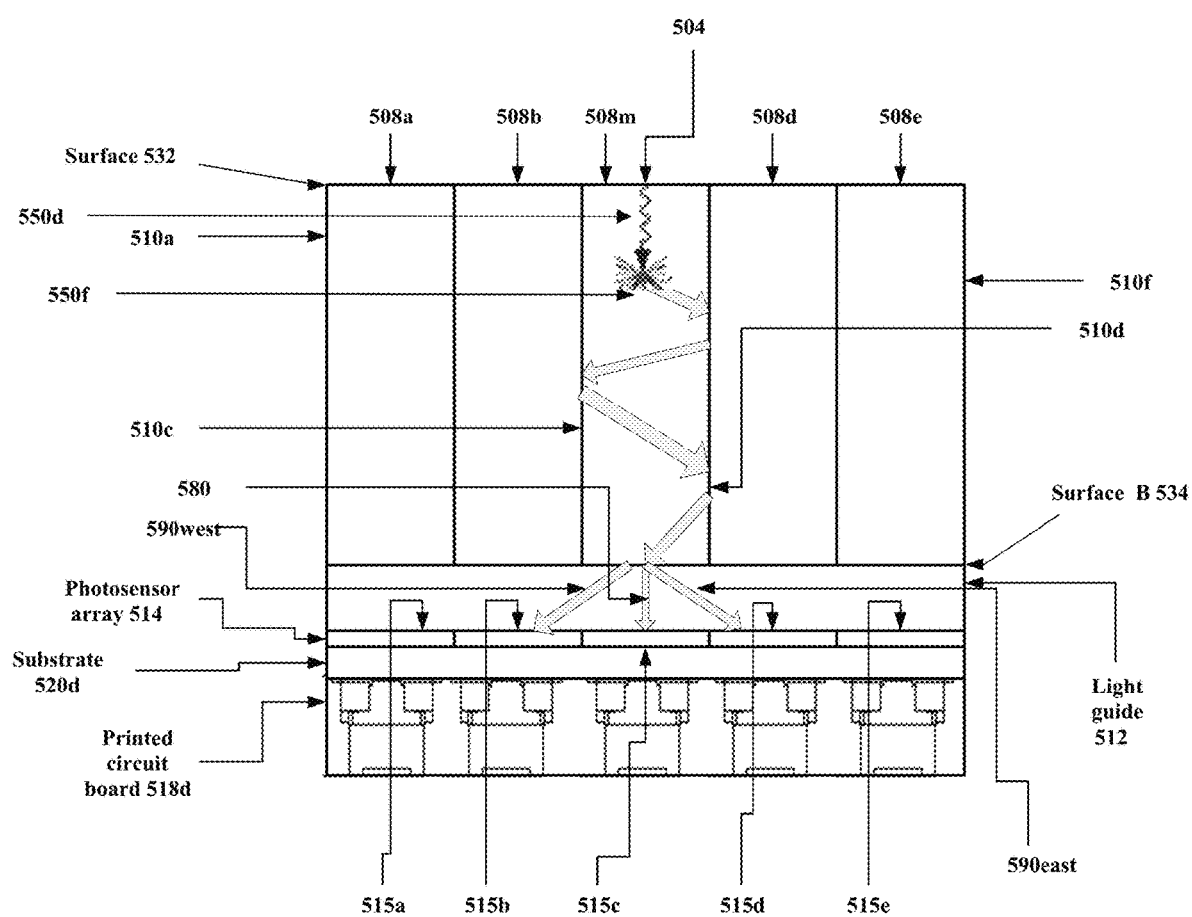

FIG. 4D further illustrates a side cross sectional view of the PET detector 500 of FIG. 4A. Specifically, FIG. 4D shows the PET detector receiving radiation photons 504 from a radiation source 502 (FIG. 4A). The radiation photons 504 enter a scintillation crystal 508m. Further, the radiation photons 504 enter into the scintillation crystal array 506 through the top reflective film 510t (not shown in FIG. 4D) and through the surface A 532 in a generally downward direction as shown by arrows 550d in FIG. 4D. The scintillation light generated by the photons 504 travels through the scintillation crystal 508m and is reflected by the reflecting films 510c and 510d and is directed towards the light guide 512. The scintillation light then travels through the transparent light guide 512 and (a) heads towards the photosensor 515c (as shown by arrow 580) and (b) spreads out in the light guide 512 as shown by east and west directional arrows $590_{west}$ and $590_{east}$, respectively while heading toward photosensors 515b and 515d adjacent to photosensor 515c. It is to be understood that scintillation light also spreads out orthogonally to the east and west directions such that it also spreads north and south. Here even if the photosensor 515c has a one on one optical coupling with the scintillation crystal 508m, a portion of the scintillation light produced by the scintillation crystal 508m is spread out on the photosensor array 514 such that the scintillation light is received not only by the photosensor 515c but also by the photosensor 515b and the photosensor 515d that are adjacent/neighboring photosensors to the photosensor 515c in the photosensor array 514.

FIG. 5 shows a flow diagram of a non-limiting example of a method for an improved photosensor light collection according to an exemplary embodiment performed by a radiation detector 200 of FIG. 2. The operations of FIG. 6 are explained with reference to FIGS. 6A-6E.

Figure 6A:
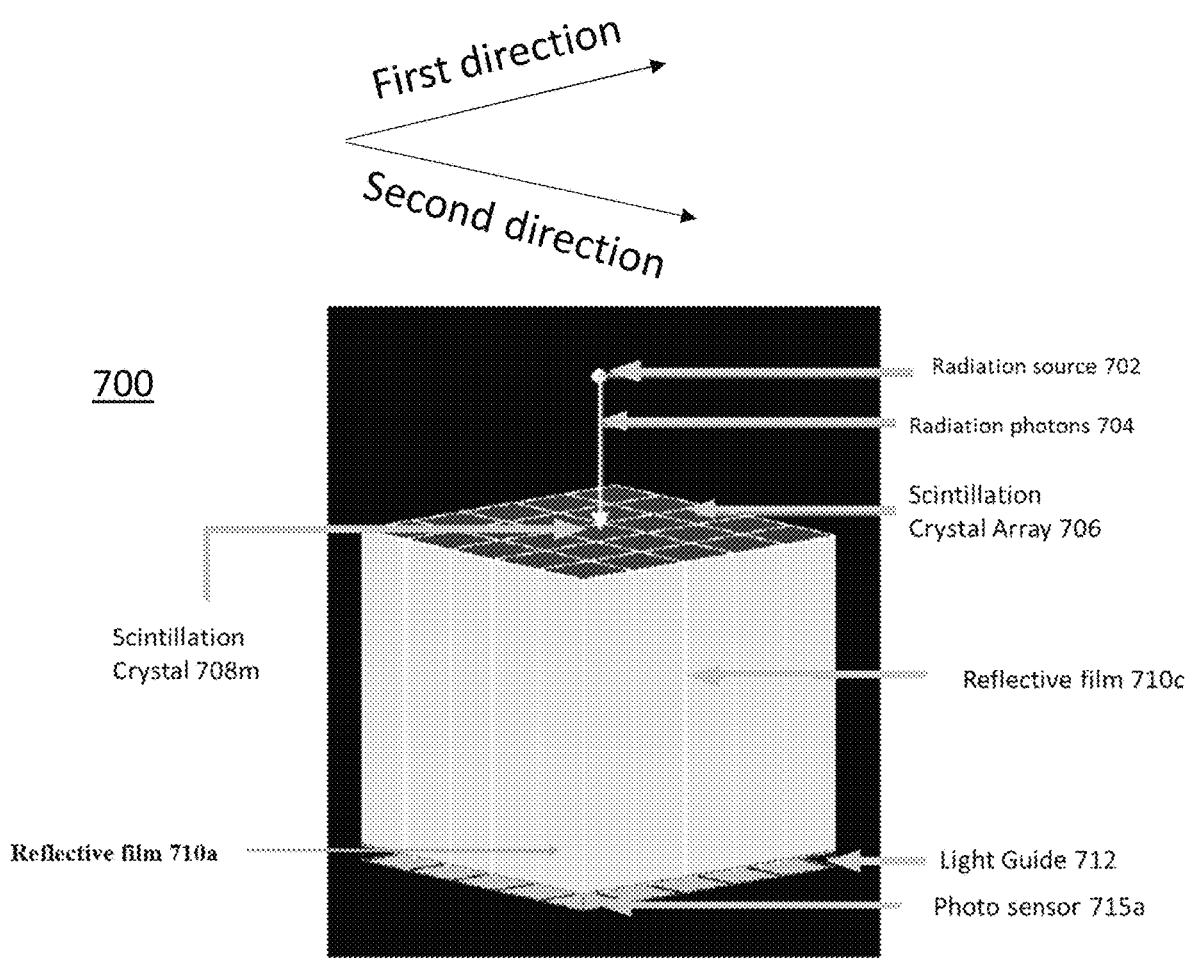
FIGS. 6A-6E are drawings illustrating an example of a structure of a scintillator array including extended reflective films.

In step 602, with reference to FIG. 6A, a PET detector 700 receives radiation photons 704 from a radiation source 702. By way of example, the PET detector 700 includes a scintillation crystal array 706 that includes a plurality of scintillation crystals (generally denoted as $708_x$) where the scintillation crystals extend in a first direction and in a second direction orthogonal to the first direction. An arbitrary scintillation crystal $708_x$ is one of the scintillation crystals of the scintillation crystal array 706, but generally examples will be described herein with respect to a middle scintillation crystal 708m. Further, reflective films (including exemplary noted reflective films 710a and 710c), a light guide 712, and a photosensor array 714 are illustrated in PET detector 700. The radiation photons 704 from the radiation source 702 are illustratively incident at the scintillation crystal 708m.

Figure 6B:
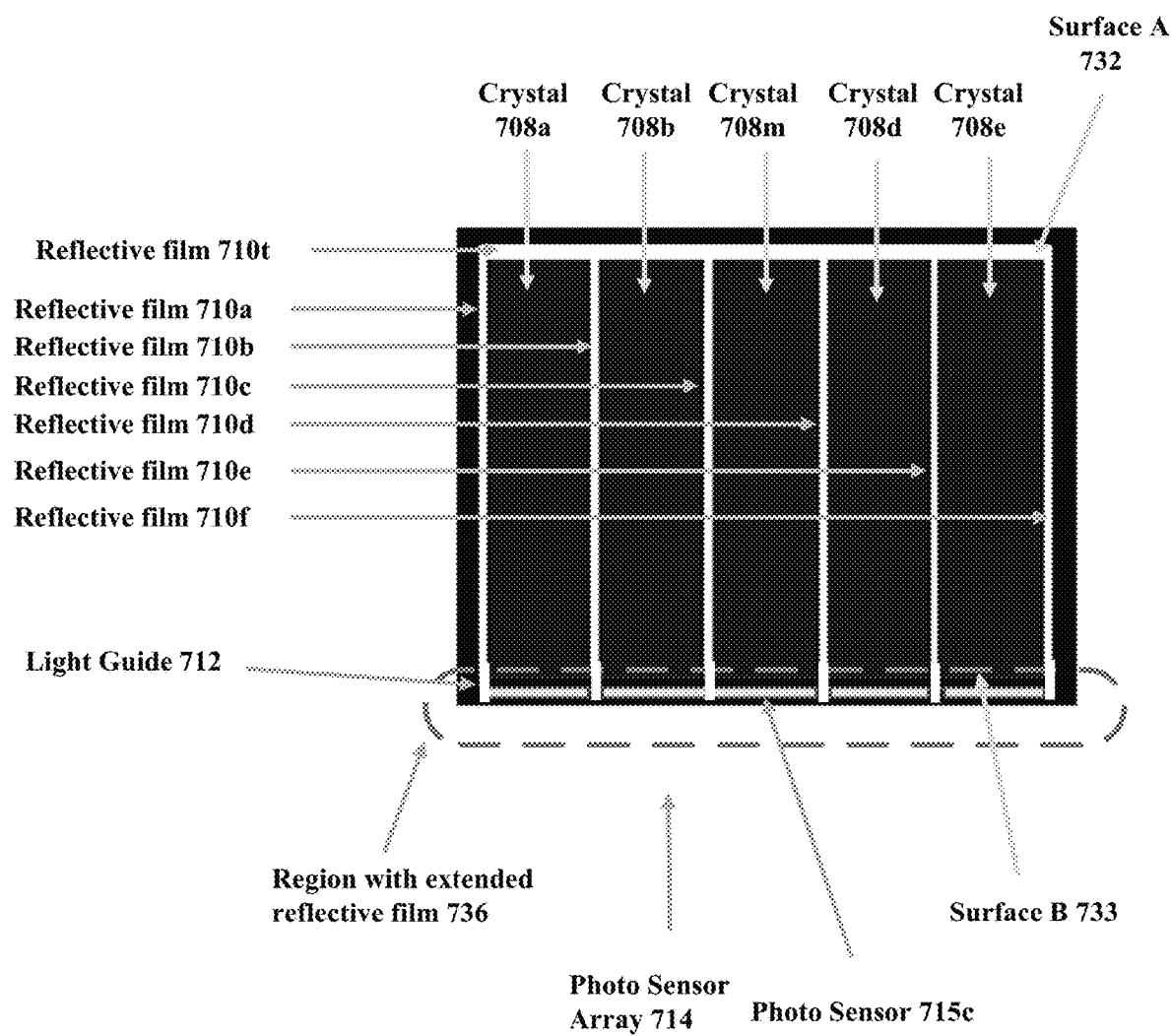

Further, FIG. 6B shows a cross sectional view of the PET detector 700 and illustrates a plurality of reflective films 710a-710f surrounding (in a first direction) a plurality of scintillation crystals 708a, 708b, 708m, 708d, and 708e of the scintillation crystal array 706. Each of the plurality of scintillation crystals 708a, 708b, 708m, 708d, and 708e are optically isolated from its neighboring scintillation crystals by respective reflective films therebetween. For example, the scintillation crystal 708b has the scintillation crystals 708a and 708c as its neighboring scintillation crystals (in the first direction) and is isolated from the scintillation crystals 708a and 708c by the reflective films 710b and 710c. As would be understood, the scintillation crystal 708b also may have up to two adjacent neighbor crystals in a second direction orthogonal to the first direction depending on whether scintillation crystal 708b is an edge crystal in the second direction.

Each of the reflective films 710a-710f may be an ESR film, a glass material, a resin material, a deposited metallic silver material, a deposited aluminum material, and/or an adhesive material mixed with Teflon particles, although any other type of reflective film may also be included, as can combinations of films. Also, not all the films need be the same type of film. For example, internal films 710b-710e may be one type of film while external films 710a and 710f may be a second type of film.

A light guide 712 is positioned in between the scintillation crystal array 706 and the photosensor array 714. The light guide 712 is utilized to distribute scintillation light from the scintillation crystal array 706 to photosensors of the photosensor array 714 positioned at the bottom surface of FIG. 6A. In one embodiment, the light guide 712 is a transparent layer made of transparent material such as glass or plastic, although other types of transparent material may also be included.

Figure 6C:
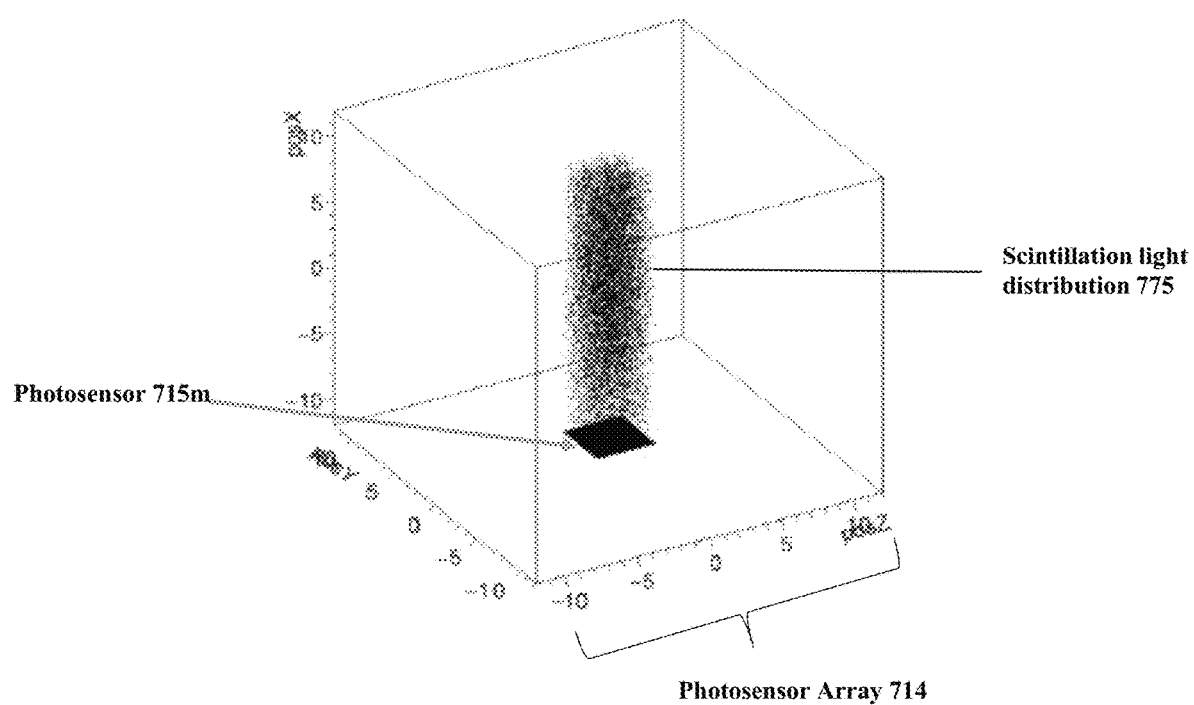

The photosensor array 714 includes a plurality of individual photosensors (any one of which is generally referenced as $715_x$), and the plurality of photosensors extend in the first and second directions in which the scintillation crystals also extend. By way of example, the individual photosensors may be SiPMs and the photosensor array 714 may be an array of a plurality of individual SiPMs. Further, the PET detector 700 has a one-to-one optical coupling between each of the scintillation crystals 708a, 708b, 708m, 708d, and 708e of the scintillation crystal array 706 and a corresponding photosensor (715a-715e) of the photosensor array 714. Each of the photosensors of the photosensor array 714 is configured to detect scintillation light from its corresponding one-to-one optically coupled scintillation crystal. FIG. 6E, explained in detail below, illustrates an example of one-to-one optical coupling between a photosensor and a scintillation crystal.

Using the configuration of FIGS. 6A-6E, a scintillation crystal 708m of a radiation detector 200 (FIG. 2) converts a portion of energy of the received radiation photons 704 to generate scintillation light (as shown in step 604 of FIG. 5). FIG. 6A shows a radiation photon 704 (e.g., a 511 keV gamma photon) hitting the scintillation crystal 708m. A portion of the energy carried by the radiation photon 704 is converted to generate the scintillation light that travels through the scintillation crystal 708m. Each of the four sides of the scintillation crystal has a reflective film disposed thereon. Also, the top end of the illustrated scintillation crystals has a reflective film disposed thereon which allows the radiation photon 704 to pass through but that prevents scintillation light from passing back out of the top of the scintillation crystals. Thus, the four sides and the top end of the scintillation crystal 708m are completely covered by the reflective films. This causes the generated scintillation light to reflect from the reflective films and flow through the scintillation crystal 708m and enter the light guide 712 without escaping the scintillation crystal 708m.

Further, FIG. 7B shows the reflective films 710a-710f, and the top reflective films 710t positioned along each of the plurality of scintillation crystals 708a, 708b, 708m, 708d, and 708e of the scintillation crystal array 706 such that they start at a first end on surface A 732 which is where the scintillation crystals 708a, 708b, 708m, 708d, and 708e start and end at a second end at surface B 734 which is below the photosensor array 714. The reflective films 710b-710e are disposed between the scintillation crystals 708a, 708b, 708m, 708d, and 708e such that the reflective films 710a and 710f are disposed on the outer surfaces of the scintillation crystals 708a and 708e, and the top reflective film(s) (710t) is/are deposed on the top end of the crystal array.

Specifically, the reflective films 710a-710f run along the scintillation crystals 708a, 708b, 708m, 708d, and 708e and extend all the way through into the light guide 712 and into the photosensor array 714. As shown by the portion of extended reflective films in region 736, the reflective films 710a-710f are longer (in a direction orthogonal to both the first and second directions) than the scintillation crystals 708a, 708b, 708m, 708d, and 708e. Specifically, the reflective films 710a-710f extend through the gaps between each of the individual photosensors (715a-715e in FIG. 6E) in the photosensor array 714, such that reflective films 710a-710f enter through the sides of each photosensor of the photosensor array 714 corresponding with scintillation crystal of the scintillation crystal array 706. Accordingly, each photosensor $715_x$ that is positioned on the photosensor array 714 would have a reflective film extending through its each of its four sides respectively.

In an embodiment, the reflective films 710a-710f run along the scintillation crystals 708a, 708b, 708m, 708d, and 708e and extend all the way through light guide 712, through the photosensor array 714, through a substrate 720, and end at the top of the PCB board (718 in FIG. 6E), such that the reflective films 710a-710f start at surface A 732 and end by touching the PCB board 718. In an alternate embodiment, the reflective films 710a-710f extend down but end inside the substrate 720 before reaching the edge of the PCB board 718.

The reflective films (surrounding the scintillator crystals $708_x$) that extend into the light guide 712 of the radiation detector 200 cause reflection of the scintillation light towards the photosensor $715_x$ that is positioned optically opposite to the scintillator crystal $708_x$ (as noted in step 606 of FIG. 5). Thus, the scintillation light from the scintillator crystal $708_x$ is received by the photosensor $715_x$ on the photosensor array 714 in a one-to-one optical correspondence.

In general, the photosensor $715_x$ detects the scintillation light only from the scintillator crystal $708_x$ and not from any neighboring scintillator crystals surrounding the scintillator crystal $708_x$ (as noted in step 608 of FIG. 5). Also, the corresponding photosensors of any neighboring scintillator crystals surrounding the scintillator crystal $708_k$ do not detect the scintillation light from the scintillator crystal $708_x$ and light from scintillator crystals adjacent to the scintillator crystal $708_x$ is not detected by the photosensor $715_k$ corresponding to the scintillator crystal $708_x$. FIG. 6C shows an exemplary simulation graph of the scintillation light received by photosensor 715m on the photosensor array 714 from the scintillator crystal 708m in a one-to-one optical correspondence. The simulation graph illustrates a scintillation light distribution 775 generated in response to simulated photons 704 hitting the scintillation crystal 708m to generate the scintillation light. Specifically, the scintillation light distribution 775 is the simulation of the amount of scintillation light received by the photosensor 715m on the photosensor array 714 from the scintillator crystal 708m in a one-to-one optical correspondence.

Figure 6D:
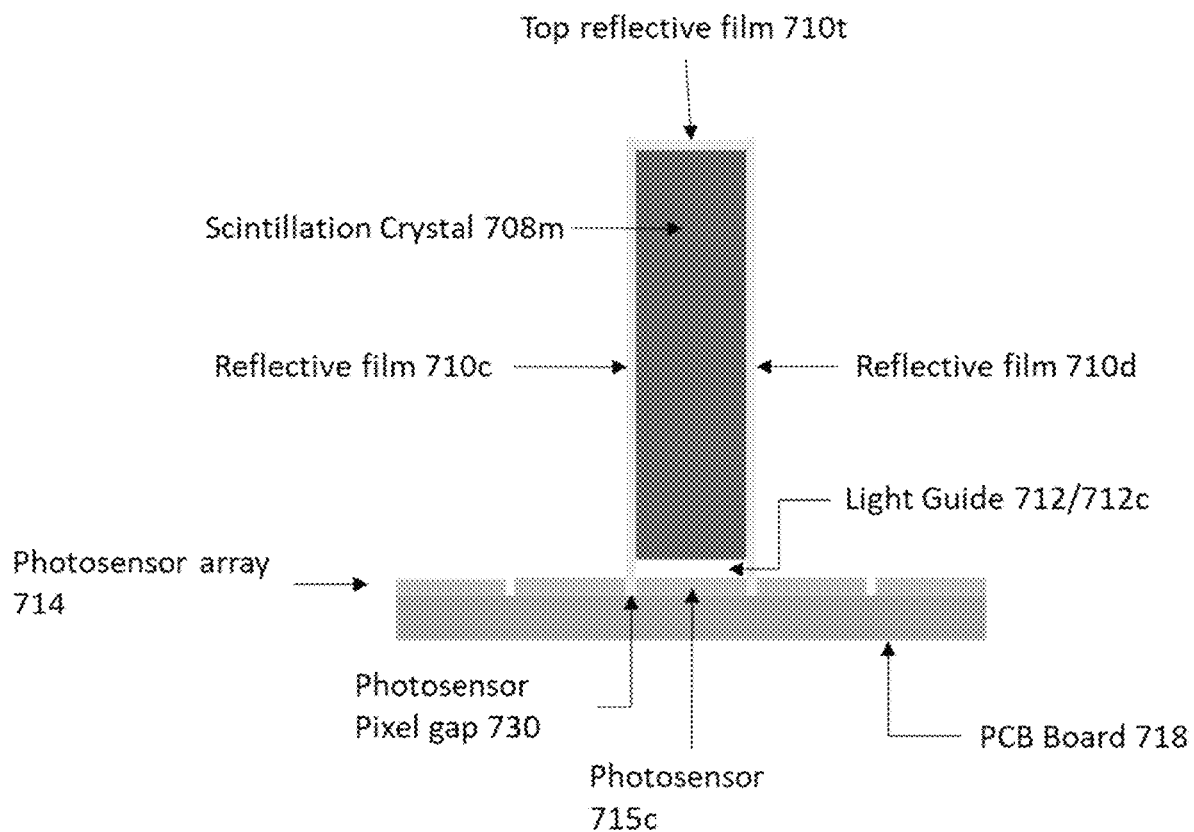
Figure 6E:
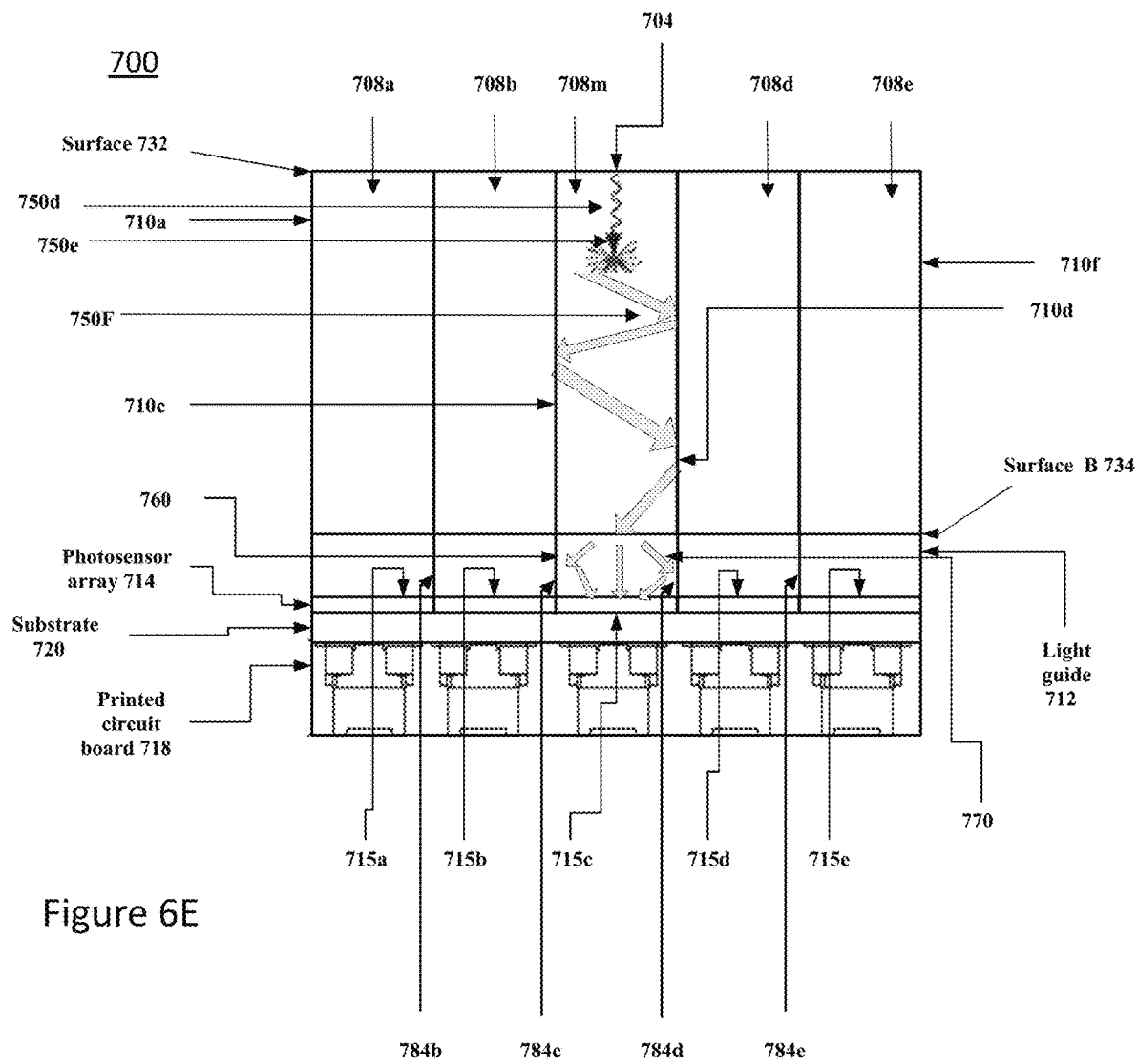

FIG. 6D is a side view of the photosensor array of the radiation detector 200 emphasizing a side view of a scintillation crystal 708m that has one-to-one optical coupling with the photosensor 715c of the photosensor array 714. The scintillation crystal 708m has a first reflective film 710c disposed on its first side and a second reflective film 710d disposed on its second side, and a third reflective film 710t disposed on its top end, the scintillation crystal 708m is optically coupled to the light guide 712, then the light guide 712 is optically coupled to the photosensor 715c of the photosensor array 714 disposed below the light guide 712. The illustrated light guide may also be referred to based on the photosensor to which it is correlated since it is isolated from portions of the light guide that couple to surrounding photosensors. Thus, the light guide corresponding to photosensor 715c may also be referred to as light guide 712c. Further a PCB board 718 is disposed below the photosensor array 714.

FIG. 6E, illustrates that the first reflective film 710c and the second reflective film 710d are disposed around the photosensor 715c and extend through the light guide 712c and the photosensor array 714 into the PCB board 718.

In an embodiment, the photosensor pixel gap 730 of FIG. 6D may be filled with reflective material. Reflective material may include enhanced specular reflector (ESR) film, a glass material, a resin material, deposited metallic silver, deposited aluminum, and/or an adhesive material mixed with Teflon particles, although any other type of reflective material may also be included, and a combination of materials also may be used.

In this embodiment, instead of extending the reflective films 710c and 710d from the light guide 712c into the photosensor array 714, the reflective films 710c and 710d would be extended through the light guide 712c through until the surface of the PCB Board 718, such that the reflective films 710c and 710d would pass through the photosensor array 714. Further, as the photosensor pixel gap 730 is filed with reflective material, the scintillation light reflects from the reflective films 710c and 710d in the light guide 712c and flows through to the 715c without escaping the scintillation crystal 708m or the photosensor pixel gap 730 or the light guide 712c. Additionally, the scintillation light from scintillation crystals neighboring the scintillation crystal 708m are not detected by photosensor 715c as the reflective films 710c and 710d would block any outside light from being detected by the photosensor 715c. Accordingly, the spreading of scintillation light and the optical light crosstalk do not take place. Thus, this configuration will increase the amount of light detected from a single scintillation crystal 708m and improve the timing/energy resolution.

FIG. 6E further illustrates a side cross sectional view of the PET detector 700. Specifically, FIG. 6E shows the PET detector 700 receiving radiation rays that include photons 704 from a radiation source. The photons 704 enter a scintillation crystal 708m. Further, the photons 704 enter through the surface A 732 into the scintillation crystal array 706 in a generally downward direction as shown by arrows 750d in FIG. 6E. The scintillation light, generated by the photons colliding (750e) with the material of the crystal, travels through the scintillation crystal 708m and is reflected by the reflecting films 710c and 710d and the top reflective film 710t and is directed towards the light guide 712. (Arrows 750f show the direction of the scintillation light within the scintillation crystal 708m.) The scintillation light then travels through the transparent light guide 712 and is directed towards the photosensor 715c. The scintillation light is directed in the light guide 712 as shown by directional arrows 760 and 770 towards the photosensor 715c. As the light guide 712 has the reflective films 784c and 784d extending from the scintillation crystal 708m through to the photosensor 715c, the scintillation light is reflected from the reflective films 710c and 710d in the scintillation crystal 708m and is further reflected in the light guide 712 by the reflective films 784c and 784d and flows through to the photosensor 715c without escaping the scintillation crystal 708m or the light guide 712. Additionally, the scintillation light from the neighboring scintillation crystals 708b and 708d do not enter the photosensor 715c and is thus not detected by photosensor 715c. Accordingly, the photosensor 715c only detects light from its corresponding one-to-one optically coupled scintillation crystal 708m and thus spreading of light and the optical light crosstalk do not take place. Thus, this technology will increase the amount of light detected from a single scintillation crystal 708m, thus improving the timing/energy resolution.

Accordingly, the reflective film pairs 710a/b, 710b/c, 710c/d, 710d/e, and 710e/f within the light guide 712 provide reflection of the scintillation light in the light guide 712 from the scintillation crystals 708a, 708b, 708m, 708d, and 708e towards their corresponding one-to-one optically coupled photosensors 715a, 715b, 715c, 715d, 715e, respectively.

In another embodiment, instead of filing the photosensor pixel gap 730 with reflective material, a reflective material is applied to the edges of the packaging of the individual photosensors of the photosensor array 714 before assembling of the photosensor array 714.

Figure 7:
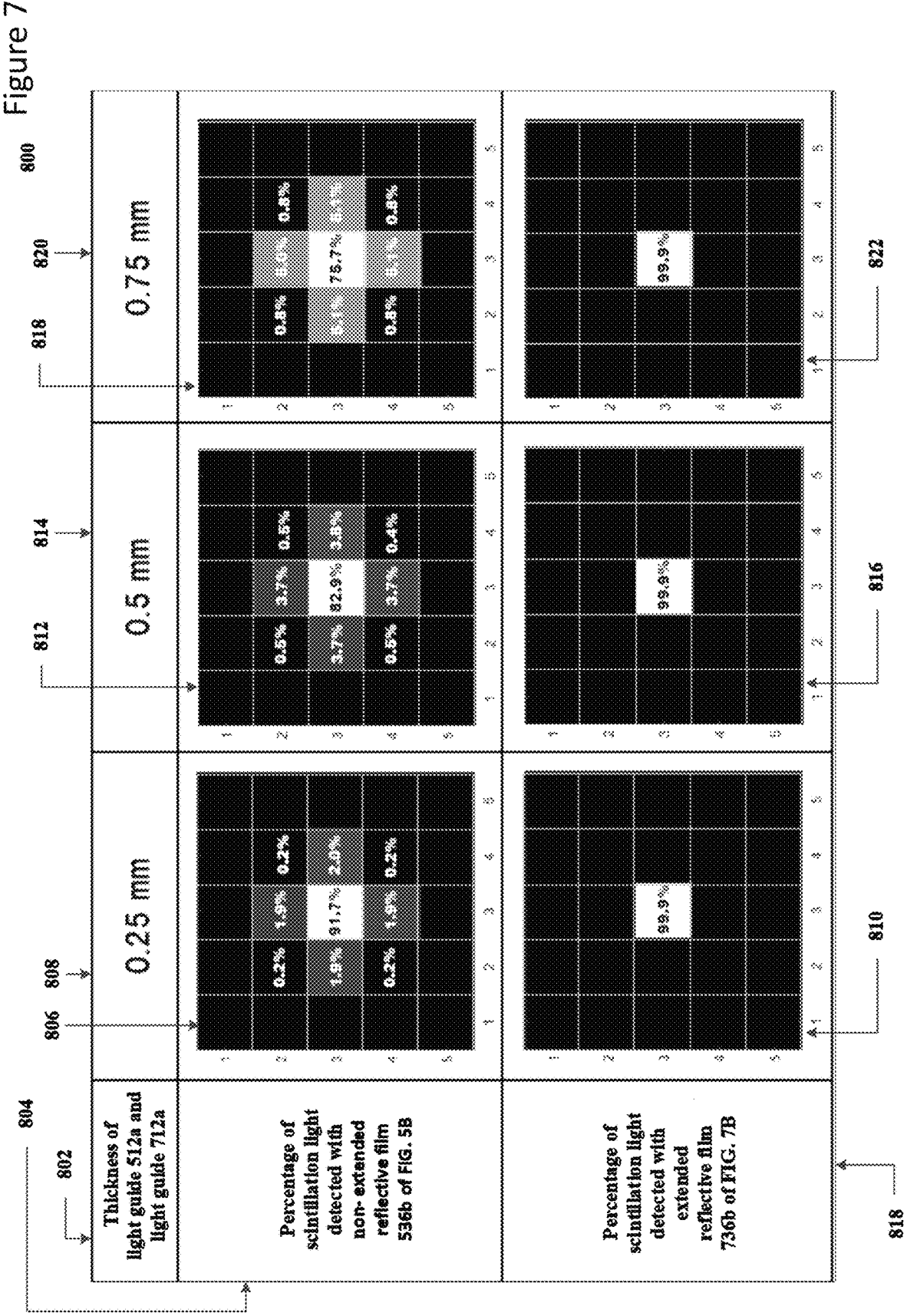
FIG. 7 illustrates a graphical representation of amounts of scintillation light detected.

FIG. 7 illustrates a table 800 of percentages of the scintillation light detected by the photosensor array 514 with reference to FIG. 4B and by the photosensor array 714 with reference to FIG. 6B. Table 800 shows a row 802 for thickness values of the light guide 512 and the light guide 712. Specifically, FIG. 7 illustrates a percentage of scintillation light detected 804 by the photosensor array 514 when the associated light guide 512 is simulated to have three different thickness conditions (0.25 mm, 0.5 mm, and 0.75 mm) with reference to FIG. 4B and does not have any reflective films extended into the light guide 512 (as indicated by the absence of an extended reflective film in the region 536).

Additionally, table 800 also illustrates a simulated percentage of the scintillation light detected 820 by the photosensor array 714 when the associated light guide 712 has three different thickness conditions (0.25 mm, 0.5 mm, and 0.75 mm) using a configuration such as in FIG. 6B where the reflective films extend into the light guide 712 (indicated by the portion of extended reflective film 736).

The graphical representation 806 indicates that when using a 0.25 mm light guide 512a, the photosensor 515c positioned in the middle of the photosensor array 514 detects 91.7% percentage of scintillation light and further indicates that the eight neighboring photosensors that surround the photosensor 515c in a clockwise direction detect 1.9%, 0.2%, 2.0%, 0.2%, 1.9%, 0.2%, 1.9%, and 0.2% of the scintillation light generated in the simulation. As, the eight neighboring photosensors that surround the photosensor 515c detect the scintillation light that should have been directed to the photosensor 515c, this indicates that there is optical light crosstalk between the photosensor 515c and the eight neighboring photosensors that surround the photosensor 515c.

By contrast, the graphical representation 822 indicates that the photosensor 715c positioned in the middle of the photosensor array 714 detects 99.9% percentage of the scintillation light generated in the simulation and further indicates essentially no scintillation light being detected by any other of the photosensors surrounding the photosensor 715c in the photosensor array 714 (regardless of the which of the three thicknesses is used). As, the eight neighboring photosensors that surround the photosensor 715c do not detect any appreciable scintillation light that should have been directed to the photosensor 715c, this indicates that there is no appreciable optical light crosstalk between the photosensor 715c and the eight neighboring photosensors that surround the photosensor 715c.

FIG. 7 illustrates a graphical representation 814 indicating that the photosensor 515c positioned in the middle of the photosensor array 514 detects a decreasing percentage of the generated scintillation light as the thickness of the light guide 512 increases. For example, for a thickness of 0.5 mm, 82.9% percentage of the scintillation light is detected at the photosensor 515c positioned in the middle, and the eight neighboring photosensors that surround the photosensor 515c in a clockwise direction detect 3.7%, 0.5%, 3.8%, 0.4%, 3.7%, 0.5%, 3.7%, and 0.5% of scintillation light, respectively. When the light guide thickness is increased to 0.75 mm, the percentage of the scintillation light detected at the photosensor 515c positioned in the middle drops even further to 75.7%.

Figure 8:
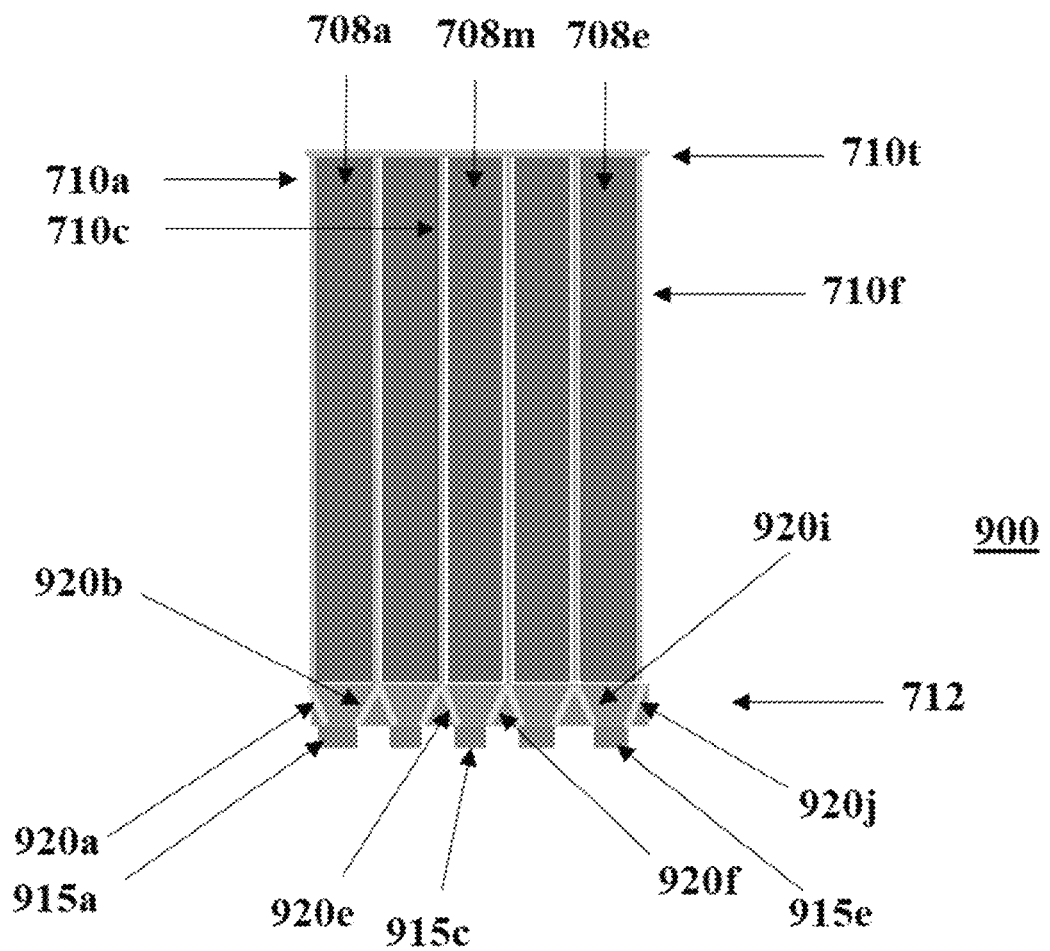
FIG. 8 illustrates an example of a structure of the scintillator array including extended and tilted reflective films passing through the light guide.

FIG. 8 illustrates a cross sectional view of a modified radiation detector 200 of FIG. 2. Specifically, FIG. 8 is a cross sectional view of PET detector 900 that includes scintillation crystals 708a, 708b, 708m, 708d, and 708e that together form part of a scintillation crystal array. Each of the scintillation crystals 708a, 708b, 708m, 708d, and 708e is surrounded by a corresponding reflective films 710a-710f and a top reflective film 710t. Further, the PET detector 900 includes a light guide layer 712 that forms a layer on the bottom of the scintillation crystals 708a, 708b, 708m, 708d, and 708e. Below the light guide layer 712 is a layer of photosensor arrays including photosensors 915a, 915c, and 915e (with the other photosensors not being labeled for clarity). Each of the scintillation crystals 708a, 708m, and 708e forms a one-to-one coupling with a corresponding one of the photosensors 915a, 915c, and 915e, respectively, as do the other unlabeled crystals and photosensors. Further, each of the illustrated photosensors (including photosensors 915a, 915c, and 915e) has a width smaller than a width of the end of the corresponding scintillation crystal facing the layer of the photosensor arrays. Further, each of the scintillation crystals (including labeled crystals 708a, 708m, and 708e) has the same width. Also, the each of the illustrated photosensors has the same width as each other (or substantially the same width).

Each of the reflective films 710a-710f extends to the light guide 712, but the reflective films at or near the lightguide/crystal interface meet or are joined to tilted reflective films that tilt toward the respective photosensors (e.g., 915a, 915c, and 915e). For example, tilted reflective films 920a and 920b direct light from crystal 708a toward photosensor 915a. Similarly, tilted reflective films 920e and 920f direct light from crystal 708m toward photosensor 915c, and tilted reflective films 920i and 920j direct light from crystal 708e toward photosensor 915e.

Figure 9:
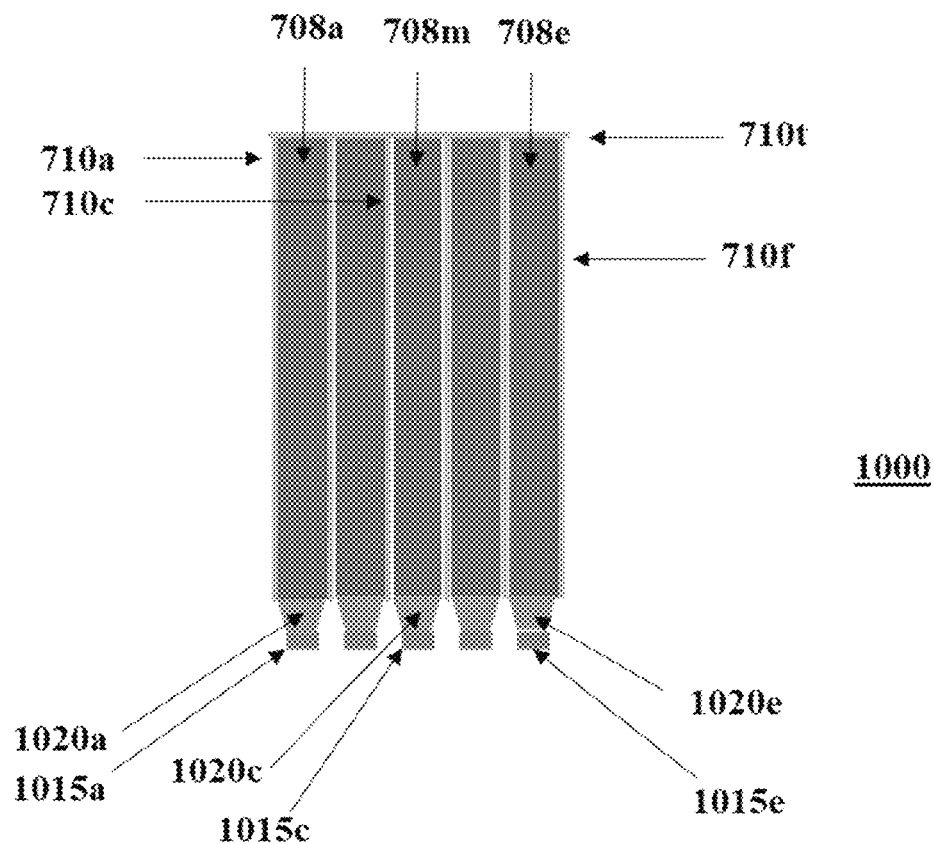
FIG. 9 illustrates an example of a structure of the scintillator array including a lens acting as an enhanced light guide.

FIG. 9 illustrates a cross sectional view 1000 of the radiation detector 200 of FIG. 1 for an enhanced light guide layer. Specifically, FIG. 9 is a cross sectional view of PET detector 1000 that has a scintillation crystal array as discussed above with respect to FIGS. 6A-6E and 9. Further, the PET detector 1000 includes a photosensor array including a plurality of photosensors extending in the first and second orthogonal directions. FIG. 9 illustrates three labeled photosensors 1015a, 1015c, and 1015e, but two other unlabeled photosensors. Each of the scintillation crystals (including labeled crystals 708a, 708m, and 708e) forms a one-to-one coupling with a corresponding photosensor. Each of the photosensors has a width smaller than the width of the corresponding scintillation crystal facing the photosensor array. Further, an enhanced light guide layer is included between the scintillation crystals array and photosensor array of the radiation detector 200.

The enhanced light guide layer includes individual light guide lenses including labeled lenses 1020a, 1020c, and 1020e. The light guide lenses may include a Fresnel type of lens, although other lens types similarly also may be used. Each of the light guide lenses optically couple a corresponding scintillation crystal (e.g., 708m) to a corresponding photosensor (e.g., 1015c). Photosensors 1015a and 1015e similarly are coupled to crystals 708a and 708e, respectively, by lenses 1020a and 1020e. As illustrated in FIG. 9, the widths of the light guide lenses (including labeled lenses 1020a, 1020c, and 1020e) are larger closer to their corresponding crystals than they are closer to their corresponding photosensors.

In another embodiment, a reflective layer is etched into the light guide 712 by using laser dicing techniques. Alternatively, laser etching can be replaced with reflective films. FIG. 11 shows a structure 100 of the scintillator array including laser etched reflective layer within a light guide. FIG. 11 shows the light guide 712 is laser etched to act as reflective regions. By way of example, FIG. 10 shows 1110b, 1110c, 1110d, and 1110e as reflective regions that are laser etched in the light guide 712.

Figure 10:
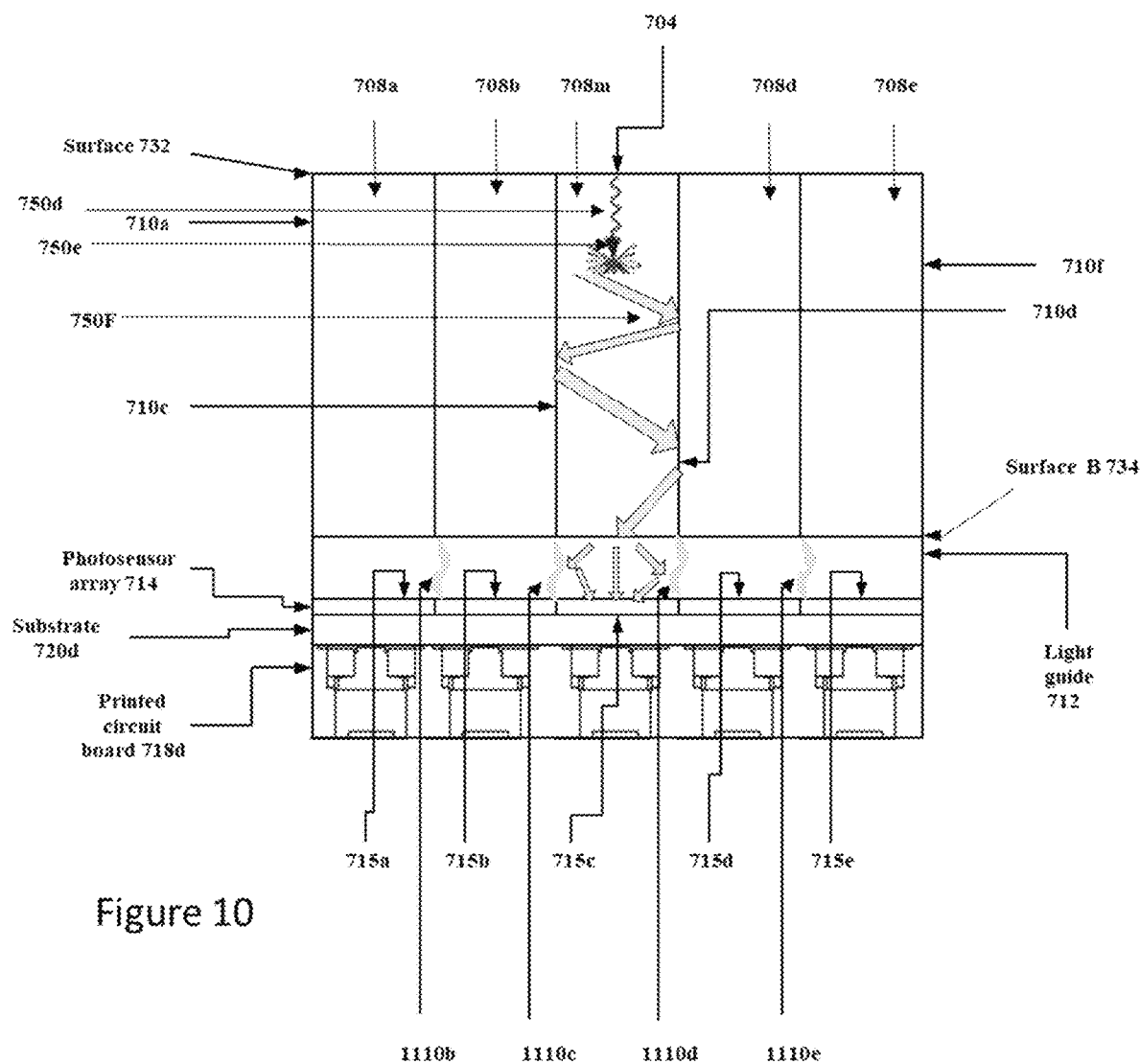
FIG. 10 illustrates an example of a structure of the scintillator array including laser etched reflective barriers within a light guide.

Specifically, FIG. 10 shows the radiation rays 704 enter into the scintillation crystal array 706 through the surface A 732b in a generally downward direction as shown by arrows 750e in FIG. 10. The scintillation light generated by the photons travels through the scintillation crystal 708m and is reflected by the reflecting films 710a and 720b and the top reflective film and is directed towards the light guide 712 (arrows 750f shows the direction of the scintillation light within the scintillation crystal 708m). The scintillation light then travels through the light guide 712 that is transparent and is reflected by the reflective regions of the laser etches 1110b, 1110c, 1110d, and 1110e in the light guide 712 causing the scintillation light to be received only by the photosensor 736c that is one on one optically coupled to scintillation crystal 708a.

Further, the constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

With regard to the processes explained in the embodiments and the modification examples described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to provide a radiation detector, a medical image diagnosis apparatus, a method of an improved photosensor light collection, and a radiation detector apparatus.

Embodiments of the present disclosure may also be as set forth in the following parentheticals.

(1) A radiation detector apparatus, comprising: a scintillator array comprising a first scintillator crystal and a plurality of second scintillator crystals adjacent to the first scintillator crystal within the scintillator array; a photosensor array comprising a first photosensor which is coupled in a one-to-one relationship with the first scintillator crystal; and a first separator positioned between the first scintillator crystal and the plurality of second scintillator crystals, wherein the first separator optically separates the first scintillator crystal and the plurality of second scintillator crystals such that the first photosensor detects photons from the first scintillator crystal and not from the plurality of second scintillator crystals in the scintillator array.

(2) The radiation detector apparatus of (1), further comprising: a light-guide, positioned between the scintillator array and the photosensor array wherein the first separator is positioned within the light-guide between the first scintillator crystal and the plurality of second scintillator crystals.

(3) The radiation detector apparatus of any one of (1) to (2), wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

(4) The radiation detector apparatus of (4), further comprising: a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

(5) The radiation detector apparatus of any one of (1) to (5), wherein the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, and a reflective film.

(6) A medical image diagnosis apparatus comprising: a scintillator array comprising a first scintillator crystal and a plurality of scintillator crystals adjacent to the first scintillator crystal within the scintillator array; a photosensor array comprising a first photosensor which is coupled in a oneto-one relationship with the first scintillator crystal; and a first separator positioned between the first scintillator crystal and the plurality of second scintillator crystals, wherein the first separator optically separates the first scintillator crystal and the plurality of second scintillator crystals such that the first photosensor detects photons from the first scintillator crystal and not from the plurality of second scintillator crystals in the scintillator array.

(7) The medical image diagnosis apparatus of (7), further comprising: a light-guide, positioned between the scintillator array and the photosensor array wherein the first separator is positioned within the light-guide between the first scintillator crystal and the plurality of second scintillator crystals.

(8) The medical image diagnosis apparatus of any one of (7) to (8), wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

(9) The medical image diagnosis apparatus of (10), further comprising: a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

(10) The medical image diagnosis apparatus of (7), wherein the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, and a reflective film.

(11) A method of an improved photosensor light collection, the method comprising: receiving incident radiation by a scintillator array comprising a first scintillator crystal and a plurality of scintillator crystals adjacent to the first scintillator crystal within the scintillator array, detecting photons by a photosensor array from the first scintillator crystal, wherein the photosensor array comprising a first photosensor which is coupled in a one-to-one relationship with the first scintillator crystal, wherein a first separator positioned between the first scintillator crystal and the plurality of second scintillator crystals, the first separator is configured to optically separate the first scintillator crystal and the plurality of second scintillator crystals such that the first photosensor detects photons from the first scintillator crystal and not from the plurality of second scintillator crystals in the scintillator array.

(12) The method of either of (13) or (14), wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

(13) The method of (13), wherein the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, and a reflective film.

(14) The radiation detector apparatus of (1), wherein each of the plurality of photosensors are configured based on one to one correspondence to detect photons from a corresponding one of the plurality of scintillator crystals.

(15) The medical image diagnosis apparatus of (7), wherein each of the plurality of photosensors are configured based on one to one correspondence to detect photons from a corresponding one of the plurality of scintillator crystals.

(16) The method of (13), wherein each of the plurality of photosensors are configured based on one to one correspondence to detect photons from a corresponding one of the plurality of scintillator crystals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiation detector apparatus, comprising:
   a scintillator array comprising a first scintillator crystal and a plurality of second scintillator crystals adjacent to the first scintillator crystal within the scintillator array;
   a photosensor array comprising a first photosensor which is coupled in a one-to-one relationship with the first scintillator crystal;
   a light-guide positioned between the scintillator array and the photosensor array; and
   a first separator positioned between the first scintillator crystal and the plurality of second scintillator crystals, positioned between the first scintillator crystal and the plurality of second scintillator crystals within the light-guide, and positioned around the first photosensor, wherein the first separator is an optical reflector.

2. The radiation detector apparatus according to claim 1, wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

3. The radiation detector apparatus according to claim 2, further comprising:
   a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

4. The radiation detector apparatus according to claim 1, wherein the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, and a reflective film.

5. A medical image diagnosis apparatus comprising:
   a scintillator array comprising a first scintillator crystal and a plurality of second scintillator crystals adjacent to the first scintillator crystal within the scintillator array;

a photosensor array comprising a first photosensor which is coupled in a one-to-one relationship with the first scintillator crystal;

a light-guide positioned between the scintillator array and the photosensor array; and a first separator positioned between the first scintillator crystal and the plurality of second scintillator crystals, positioned between the first scintillator crystal and the plurality of second scintillator crystals within the light-guide, and positioned around the first photosensor, wherein the first separator is an optical reflector.

6. The medical image diagnosis apparatus according to claim 5, wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

7. The medical image diagnosis apparatus according to claim 6, further comprising:

a second separator positioned between the first scintillator crystal and the third scintillator crystal, wherein the second separator optically separates the first scintillator crystal and the third scintillator crystal such that the first photosensor detects photons from the first scintillator crystal and not from the third scintillator crystal.

8. The medical image diagnosis apparatus according to claim 5, wherein the first separator is at least one of (a) a reflective layer cut into a light guide using laser dicing and (b) a reflective material selected from the group consisting of: a glass material, a resin material, deposited metallic silver, deposited aluminum, Teflon particles mixed with an adhesive material, and a reflective film.

9. A method of an improved photosensor light collection, the method comprising:

receiving incident radiation by a scintillator array comprising a first scintillator crystal and a plurality of second scintillator crystals adjacent to the first scintillator crystal within the scintillator array, detecting photons by a photosensor array from the first scintillator crystal, wherein the photosensor array comprising a first photosensor which is coupled in a one-to-one relationship with the first scintillator crystal, wherein a first separator positioned between the first scintillator crystal and the plurality of second scintillator crystals, positioned between the first scintillator crystal and the plurality of second scintillator crystals within a light-guide, and positioned around the first photosensor, wherein the first separator is an optical reflector.

10. The method according to claim 9, wherein the plurality of second scintillator crystals includes a second scintillator crystal and a third scintillator crystal, and wherein the first scintillator crystal and the second scintillator crystal are adjacent to each other in a first direction and the first scintillator crystal and the third scintillator crystal are adjacent to each other in a second direction perpendicular to the first direction.

11. The method according to claim 9, wherein the first separator is at least one of (a) a reflective layer cut into a light guide using laser dicing and (b) a reflective material selected from the group consisting of a glass material, a resin material, deposited metallic silver, deposited aluminum, Teflon particles mixed with an adhesive material, and a reflective film.

12. The radiation detector apparatus according to claim 1, wherein the first separator is configured to optically separate the first scintillator crystal and the plurality of second scintillator crystals such that the first photosensor detects photons from the first scintillator crystal and not from the plurality of second scintillator crystals in the scintillator array.

13. The medical image diagnosis apparatus according to claim 5, wherein the first separator is configured to optically separate the first scintillator crystal and the plurality of second scintillator crystals such that the first photosensor detects photons from the first scintillator crystal and not from the plurality of second scintillator crystals in the scintillator array.

14. The method according to claim 9, wherein the first separator is configured to optically separate the first scintillator crystal and the plurality of second scintillator crystals such that the first photosensor detects photons from the first scintillator crystal and not from the plurality of second scintillator crystals in the scintillator array.

* * * * *